United States Patent [19]

Pearce et al.

[11] 4,066,969
[45] Jan. 3, 1978

[54] MULTIPLE SHEET DETECTING APPARATUS

[75] Inventors: Phillip W. Pearce; Robert J. Hutchison, both of Rochester, N.Y.

[73] Assignee: Eastman Kodak Company, Rochester, N.Y.

[21] Appl. No.: 615,651

[22] Filed: Sept. 22, 1975

[51] Int. Cl.² .................. B65H 7/12; G08C 27/00; G08B 21/00
[52] U.S. Cl. .................. 328/5; 328/133; 271/263; 340/259
[58] Field of Search .................. 328/125, 5, 133; 250/559; 340/259; 271/258, 260, 262

[56] References Cited

U.S. PATENT DOCUMENTS

| 3,075,053 | 1/1963 | McDonough et al. | 328/5 |
| 3,603,680 | 7/1971 | Barton | 271/57 |
| 3,778,051 | 12/1973 | Allen et al. | 271/262 |
| 3,833,816 | 9/1974 | Emura et al. | 340/259 |
| 3,851,323 | 11/1974 | Eltgen | 340/259 |

Primary Examiner—Stanley D. Miller, Jr.
Assistant Examiner—B. P. Davis
Attorney, Agent, or Firm—Raymond L. Owens

[57] ABSTRACT

A multiple sheet detecting apparatus is disclosed which includes an ultrasonic transducer responsive to a time varying electrical signal to produce a time varying ultrasonic signal which impinges upon sheet(s) at a position along a predetermined path. A second ultrasonic transducer receives a portion of the ultrasonic wave which passes through such impinged upon sheet(s) for producing a second time varying signal. Comparison means are then provided which compare the phase relationship between the time varying electrical signals and produce an indication when such phase relationship indicates a multiple sheet feed condition has occurred.

8 Claims, 2 Drawing Figures

MULTIPLE SHEET DETECTING APPARATUS

CROSS-REFERENCE TO RELATED APPLICATIONS

Reference is made to commonly assigned, copending U.S. patent application Ser. No. 481,436, filed: June 20, 1974, entitled: SYNCHRONIZING CONTROL APPARATUS FOR ELECTROPHOTOGRAPHIC APPARATUS UTILIZING DIGITAL COMPUTER, in the names of W. E. Hunt et al.

BACKGROUND OF THE INVENTION

1. Field of the Invention

This invention relates to noncontact multiple sheet detecting apparatus that utilizes ultrasonic techniques.

2. Description of the Prior Art

In many different kinds of devices such as printing presses and copy reproducing apparatus, sheets are serially fed through different work stations wherein they are operated upon. When multiple sheets are accidentally forwarded, jams may occur at processing stations which result in machine malfunctions. In these apparatus, it is important to detect when superposed sheets are fed. This is especially true with the high speed sequential sheet feeding requirement of apparatus such as some copy duplicators.

Various multiple sheet detecting apparatus have been employed in the past. Many of these employ mechanical sensors to detect the multiple sheet feed condition. See, for example, U.S. Pat. No. 3,396,965. Some mechanical systems employ roller members which sense paper thickness. With mechanical systems where moving parts are involved, there are, of course, wear problems and also the difficulty of maintaining close mechanical tolerances. Not only is this a problem due to wear, but also errors can occur when sheets of material of nonuniform thickness are fed, or if a sheet is momentarily bowed when passing by a mechanical multiple sheet sensor.

Noncontact multiple sheet detecting apparatus provide a number of advantages over the mechanical contact-type systems. In one such detector disclosed in Canadian Pat. No. 929,632, a multiple sheet feed condition is determined by measuring the transmittance of light of the sheet(s) being fed and computing the difference in transmittance of such sheet(s) with respect to a reference transmittance provided relative to a sample sheet. Although such an apparatus would be effective, a problem exists in that if the transmittance of the sheet(s) being fed should change, then, the reference would have to be changed. Moreover, if the light sources should differently vary in intensity of illumination, then errors can possibly develop. Another similar electro-optical system is disclosed in U.S. Pat. No. 3,614,419 wherein the transmittance of successively fed sheets are compared to determine if there has been a double sheet condition.

Sheet detectors often determine the average transmittance of a sheet(s) to determine a multiple feed condition. However, if certain sheets that are fed have large dark pictures formed thereon or are covered with printed material while others are plain paper, it is difficult to utilize average transmittance to detect multiple sheet feeds. Moreover, electro-optical systems often require homogeneous optical density in the fed sheets; and reliable operation of such a system can be effected by color or printing on the sheets. Further, a clean optical path is often a necessity; thereby requiring further means for insuring a dirt, dust-free environment.

It should be noted that prior multiple sheet detectors of both the contacting and noncontacting variety are ineffective if intermixed sheets of paper of various thicknesses are to be fed along a path.

SUMMARY OF THE INVENTION

Accordingly, it is an object of the invention to provide an improved multiple sheet detecting apparatus of the noncontact variety which eliminates the problems found in prior art multiple sheet electro-optical apparatus.

A further object of the invention is to provide noncontact multiple sheet detecting apparatus which operates over a broad range of paper thicknesses irrespective of whether the sheets to be fed (1) include sheets of significantly different thicknesses, and/or (2) are colored or have printing or variations in optical density or have holes or perforations punched therein.

A still further object of the invention is to provide a multiple sheet detecting apparatus which performs effectively in environments in which are present noise, dust, and dirt.

Another object of the invention is to provide a multiple sheet detecting apparatus in which temperature and humidity have little, if any, effect on reliable operation.

Yet another object of the invention is to provide a multiple sheet detector which can reliably detect multiple sheet feed conditions irrespective of the type or amount of printed material on either or both sides of fed sheets.

In accordance with the disclosed embodiment of the invention, there is provided aligned first and second ultrasonic transducers which are spaced to permit sheets to be advanced between them along a predetermined path. The first transducer in response to an electrical time varying signal produces an ultrasonic wave signal which impinges upon sheet(s), and the second transducer in response to at least a portion of the ultrasonic wave which impinged upon sheet(s) produces a second time varying signal. Comparison means are then provided to be responsive to these electrical signals for comparing their phase relationships and produce an output signal when a multiple sheet feed condition has occurred.

In a preferred embodiment, a first time varying electrical signal is applied to the first transducer; and when no obstructions exist (such as fed sheet(s)) in the air gap therebetween transducers, an electrical signal is provided by the receiver transducer which is displaced in time (phase) from the first electrical signal. This initial phase shift is dependent upon the air gap between the transducers, the frequency of the signal, and the geometry of the transducers, and may be used as a normalizing base line. When a single sheet of paper is introduced into the air gap between the tranducers, the phase shift increases by say 90° or greater. If a multiple sheet is introduced, the phase shift will increase still further. The present invention is adapted to detect this further increase in phase shift and indicate that a multiple sheet feed condition has occurred. It is important to note that the present invention is not dependent upon signal intensity either of the input electrical sinusoidal signal or of the ultrasonic signal. The attenuation of the ultrasonic signal upon the insertion of a single sheet between the transducers is quite severe (may be in the order of 60dB). However, it has been observed that upon the insertion of multiple sheets this attenuation is not much greater. In any case, phase shift is not substantially dependent upon sheet thickness.

Thus, it is an important feature of the invention that by detecting the amount of phase shift, it is possible to provide an indication of whether there is a no paper, a single sheet, or a multiple sheet feed condition.

A further feature is that acoustic systems in accordance with the invention can provide reliable multiple sheet feed detecting using low cost, compact, and long-life components which can be readily adapted to a broad range of products involving sheet feed operations such as, for example, the following: paper mills, electrographic copying apparatus, punch card feeders, check transporters, or the like. Not only that, but the invention is not limited to the detection of sheets of paper; but for example, it will work with sheets of plastic or thin metal (i.e., shim stock).

Among the advantages of apparatus in accordance with the invention are the following:

1. It will operate over a broad range of thicknesses from say 0.002 to 0.025 inches or more.
2. It is virtually independent of optical density of sheets. It has been found that apparatus in accordance with the invention operates effectively with sheets with or without color or with or without printing on the paper.
3. It is not substantially affected by the speed of sheet feed. An embodiment of the invention has been found to effectively detect multiple sheet feed conditions of sheets (in this instance bank checks) traveling at about 190 inches per second.
4. It is not substantially affected by noisy or dirty environments.

Other objects of the invention and its various features and advantages will become apparent from the ensuing detailed description of the preferred embodiment discussed below.

DESCRIPTION OF THE PREFERRED EMBODIMENT

Figure 1:
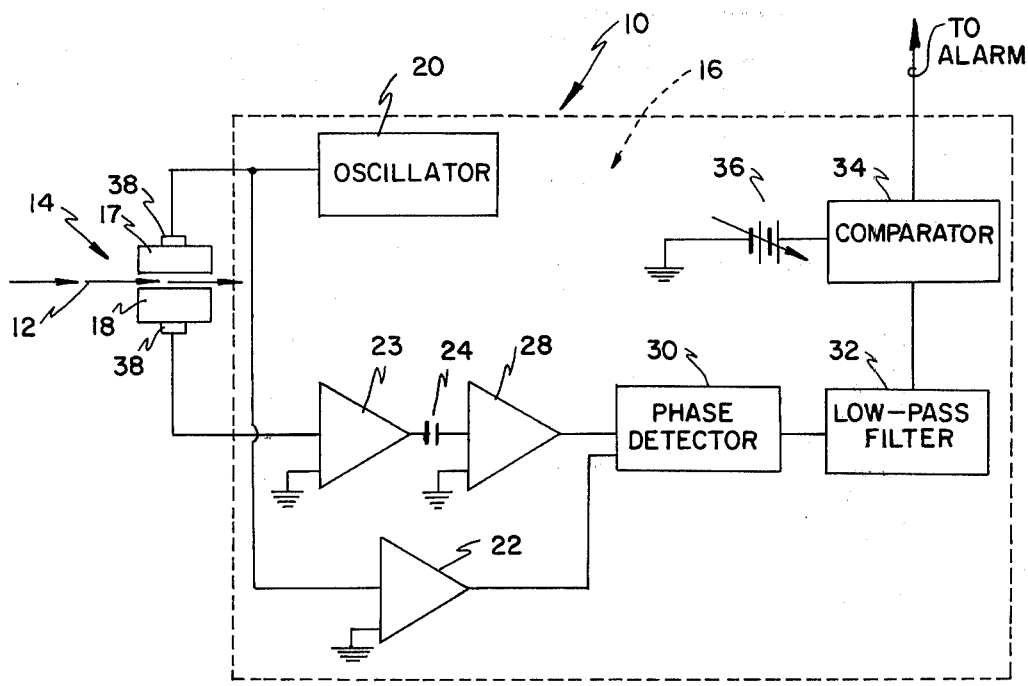
FIG. 1 is a diagrammatic representation, partially in block and partially in schematic form, showing the general arrangement of a multiple sheet detecting apparatus in accordance with the invention.

Turning now to FIG. 1, there is shown a multiple sheet detecting apparatus 10 wherein sheet(s) are advanced along a straight line path shown by arrows 12 past a sheet detector 14 and an electronic signal processor 16. The sheet detector 14 includes an ultrasonic transmitter transducer 17 and an ultrasonic receiver transducer 18 which will be discussed more fully hereafter. The signal processor includes an oscillator 20 which is directly connected to an analog comparator 22 which is adapted to provide a square wave-type output. Such a comparator is often referred to as a zero crossing comparator, and an example of one which may be used in accordance with the invention is manufactured by the National Semiconductor Corporation, 2900 Semiconductor Dr., Santa Clara, Calif. 95051, Model Number LM311. The oscillator 20 also is directly connected to the ultrasonic transmitter transducer 17. The transducer 17 produces an ultrasonic wave which impinges upon sheet(s) which pass along the path 12 between it and the receiver transducer 18. The oscillator 20 produces, for example, a sinusoidal signal (explained later) so that when there is an obstruction (such as fed sheet(s)), the receiver transducer in response to the ultrasonic signal produces an electrical signal at the same frequency as the oscillator sinusoid but shifted in phase therefrom.

Oscillator 20 may take on various forms well known in the art such as, for example, a voltage-controlled oscillator set up to operate in a self-oscillating mode at the desired frequency. An example of such an oscillator would be Model Number ICL8038 manufactured by Intersil Corporation, 10900 North Tantau Ave., Cupertino, Calif. 95014. The voltage controlled oscillator typically would provide an output to a low gain operational amplifier which in turn produces the sinusoidal signal for driving the transducer 17.

The receiver transducer is shown to be directly coupled to a wide band amplifier 23, such as a high speed operational amplifier. This amplifier may, for example, be provided by National Semiconductor Corporation Model Number LM318 which is set up in a noninverting mode. The amplifier 23 may also include a conventional L-R filter to insure that the capture range of the amplifier 23 accommodates the signal received by the receiver transducer 18. It has been found practical to have the amplifier 23 provided with a gain of approximately 300 due to the low level electrical signal produced by the transducer 18 (approximately 20mv) when a multiple sheet condition is detected by the receiver transducer 18. The output of the amplifier 23 is coupled through a capacitor 24 into a zero crossing analog comparator 28 which provides the identical function of the comparator 22 discussed above. Alternatively, the amplifier 23 could be provided by a wide bandwidth operational amplifier, for example RCA Op-Amp CA3100, manufactured by RCA Solid State, Box 3200, Somerville, N.J. 08876, again configured with a gain of 300, but with inverse parallel diodes in the feedback path. This arrangement limits signal swings to plus and minus six tenths of a volt and has the feature of improving the uniformity of the input signal to the zero crossing comparator 28.

The outputs from the comparators 22 and 28 are respectively connected to a phase comparator 30. Any conventional phase comparator, which is adapted to compare the phase of two input signals, could be used in accordance with the invention. However, it has been found that if the output of the phase detector is a square wave pulse-type output which has its positive going edge determined by the leading edge of the signal produced by the comparator 28, further signal processing can be simplified. This is so since the pulse width of the output of the phase detector will be proportional to the phase shift between the signals produced by the comparators 22 and 28 respectively. The phase detector 30 may, for a specific example, be provided by a J-K flip-flop, Model Number MC 14027, manufactured by Motorola Semiconductor Products Corporation, P.O. Box 20912, Phoenix, Ariz. 85036. When connected as a phase comparator, this Motorola flip-flop has the ability to detect phase shifts from 0° to 360° lagging.

The output pulses from the phase detector 30 are then delivered to a conventional low-pass filter 32 which may be embodied by an R-C circuit. This filter provides a DC level which is proportional to the number of sheets in the air gap between the transmitter and receiver transducer 17 and 18 respectively. The DC signal produced by the low-pass filter 32 is then delivered to a comparator 34 which also receives, as an input, a reference voltage shown as an adjustable voltage source 36. The reference level is set to correspond to that level wherein, if the DC signal from the filter 32 is above it, a multiple sheet feed condition is indicated. In such case, the comparator 34 produces an output signal which may be used to actuate an alarm line and/or turn off the machine or trigger some device such as a relay which would indicate a multiple sheet feed condition. Thus, it will be understood that the voltage of source 36 defines a range for the signal produced by the filter 32 wherein if such filter signal is in such range a multiple sheet condition will have occurred.

The reference level voltage 36 may also be determined by logic and control apparatus in accordance with a successive sheet technique. For example, for any sheet(s) that is fed, the output level of the low-pass filter could then be used to set the voltage 36 applied to the comparator 34. Now, for the next sheet(s) that is fed, a comparison can be made between the voltage 36 and the new output of the filter 32; and, if the difference between these two signals indicates a pronounced phase difference signifying a multiple sheet feed condition in either one of the two fed sheets, the alarm is sounded. If there is no such difference, the voltage 36 can be adjusted to coincide with the latest output level from the filter 32.

It should be emphasized that although the oscillator 20 is described as producing a sinusoidal signal it is not essential that a sinusoidal signal be used to practice the invention. In fact, square wave, ramp, and other time varying signals may also be used in accordance with the invention. Briefly, let us assume that a square wave-type signal is desired. In such a case, the oscillator 20 could be embodied by a phase-locked loop connected to a voltage controlled oscillator set to operate at a predetermined frequency. The output of the oscillator would then be a square wave which can conveniently be controlled to have a frequency related to the line frequency. Of course, with a square wave there is no need for the zero crossing amplifier 22 and the oscillator could be directly connected to the phase detector 30. Before the square wave signal is applied to the transducer; however, it should be filtered to remove some high frequency components. The remaining circuitry would operate in the same manner as described above.

Figure 2:
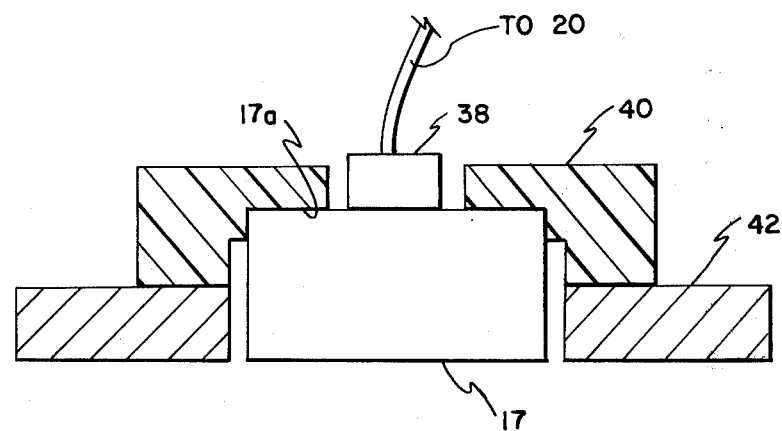
FIG. 2 is a schematic representation partially in cross section of means for mounting one of the transducers shown in FIG. 1.

Turning now to FIG. 2, there is shown one of the transducers (in this case 17) and the means for mounting same. Transducer 17 has a piezoelectric-type transducer which includes an electrical connecting jack 38 connected to the piezoelectric element within the transducer (not shown). The transducer 17 has its rear surface 17a press-fit and glued to the recessed portion of a cylindrical member 40, such member may be made of a polyvinyl chloride. Member 40 is fixedly secured to a disc-shaped member 42, preferably made of aluminum, by means of glue or by mounting screws. The member 42 is in turn secured to a machine frame (not shown) and is disposed along the path 12, as shown in FIG. 1. With this construction, only a small portion of the transducer 17 actually engages the mounting means. This is advantageous since it has been found that the sides of the transducer are set into vibration by the signal from the oscillator 20. If the sides were secured to the member 42, the signal produced by the transducer 17 could be undesirably damped.

Transducers 17 and 18 of the above-described variety are often constructed with resonant points at 23, 40, or 75 kilohertz. It has been found that transducers with resonant points at about 40 kilohertz perform very satisfactorily. Transducers which perform quite satisfactorily are a matched set of ultrasonic air transducers, Model Number 70100, Series Number 5, manufactured by Linden Laboratories, Inc., P.O. Box 920, State College, Pa. 16801. These transducers utilize a piezoelectric ceramic binder bonded to an aluminum plate.

Experimental results have shown that the phase shift is a function of the number of air-to-sheet boundaries which exist between the transducers, and the relative thickness of the papers does not have a substantial effect on the phase shift. In fact, it has been found to be virtually insignificant. Although it is not certain why this is so, the following is a plausible explanation of the physics of the situation. A physical explanation for the observed phase shift is obtained by considering the system as one of masses and springs. For instance, a sheet of paper lying parallel to and between two walls can be considered as a mass, and the layers of air above and below the paper can be considered as springs. One wall is fixed and represents the receiving transducer; the other wall, the transmitter, excites the system by being sinusoidally displaced in a direction normal to the fixed wall. The observed phase shift is the phase of the pressure at the receiver relative to the pressure at the transmitter or, in terms of the aforementioned spring-mass system, the phase of the force in the spring attached to the fixed wall, relative to the force in the spring attached to the moving wall.

This analysis does explain the fact that only the number of sheets contributes significantly to the phase shift. Viewed another way, only the boundaries between sheets and/or air substantially contribute to the phase shift phenomenon. Thus, if two sheets are actually glued together, the apparatus 10 would detect this as a single sheet (because there was no air gap). However, if the glued joint were defective and there were voids in the joint, the apparatus 10 would detect this as a multiple sheet feed condition. Thus, those skilled in the art will appreciate that the present invention may also be adapted to inspect the condition of glued joints or the like. Thus, as used herein, the term "multiple sheets" refers to a condition where sheets overlap with an air boundary between them.

It has further been found by experimentation that if the air gap between the transducers is somewhat less than 0.175 inches the air gap will not contribute significantly to the amount of phase shift. Further experiments show that the phase shift is a function of the frequency of a transmitted signal. This phase shift for zero to one and two sheets of paper increases almost linearly with sheets of paper. A specific example will now be briefly described. A matched pair of transmitter and receiver transducers, Model Number 70100, Series Number 5, manufactured by Linden Laboratories, Inc., are set to have an air gap of approximately 0.075 inches; and the oscillator 20 set to produce a sine wave at 39.106 KHz at 15 volts peak to peak. In such a case, by using 20 pound paper, the phase shifts, in terms of representative DC signal levels provided by the filter 32, are as follows:

|  | DC Signal (Filter 32) | Phase |
| --- | --- | --- |
| No Paper | 0.98v | 35.28° |

| | DC Signal (Filter 32) | Phase |
|---|---|---|
| 1 Sheet | 4.6 – 5.3v | 165.6° – 190.8° |
| 2 Sheets | 7.8 – 8.3v | 273.6° – 298.8° |

With this example, the reference voltage 36 could be selected at 6.5 volts DC. In this case, anytime the filter output is above 6.5 volts, the comparator would produce a signal indicating a multiple sheet feed condition.

It will be understood that the resonant frequency of the transducers 17 and 18 may vary from unit to unit such that the comparator 34 may have to be adjusted for any given set of transducers.

The invention has been described in detail with particular reference to a preferred embodiment thereof, but it will be understood that variations and modifications can be effected within the spirit and scope of the invention. For a specific example, next to the transducers, downstream from the direction of paper travel, a photo diode may be provided. The photo diode could act as a switch, enabling the electronics only when the entire surface of the transducers was covered by paper thereby eliminating the "edge" effects (sporadic, erroneous indications which may occur when the edge of paper crosses the surface of the transducers).

We claim:

1. Apparatus for detecting the presence of multiple sheets moving along a predetermined path, comprising:
   a. means for producing a first time varying electrical signal;
   b. first transducer means disposed on one side of the path and responsive to said first time varying signal for producing a time varying ultrasonic signal which impinges upon sheet(s) at a first position along the path;
   c. second transducer means disposed on the opposite side of the sheet path and aligned with said first transducer means to receive at least a portion of the ultrasonic wave which impinged upon said sheet(s) for producing a second time varying electrical signal; and
   d. phase comparison means responsive to said first and second time varying electrical signals for comparing their phase relationship and producing an output signal when such phase relationship indicates a multiple sheet feed condition has occurred.

2. The invention as set forth in claim 1 wherein said phase comparison means includes:
   i. a first zero crossing comparator responsive to said second time varying signal for producing a first square wave-type output;
   ii. phase detector means responsive to said first square wave signal and said first time varying signal for producing a pulse-type signal, the width of which is a function of the phase difference between said first and second time varying signals;
   iii. a low-pass filter connected to said phase detector means; and
   iv. output comparator means connected to said low-pass filter for providing an indication when a multiple sheet feed condition has occurred.

3. The invention as set forth in claim 2 wherein said output comparator means includes an adjustable reference voltage source.

4. Apparatus for detecting the presence of multiple sheets moving along a predetermined path, comprising:
   a. means for producing a first time varying electrical signal;
   b. first transducer means disposed on one side of the path and responsive to said first time varying signal for producing a time varying ultrasonic signal which impinges upon sheet(s) at a first position along the path;
   c. second transducer means disposed on the opposite side of the sheet path and aligned with said first transducer means to receive at least a portion of the ultrasonic wave which impinged upon said sheet(s) for producing a second time varying electrical signal;
   d. means responsive to said first and second time varying signals for producing a third electrical signal having a parameter which is a function of the difference between the phases of such first and second signals;
   e. means for producing a reference signal having a parameter which defines a range of parameters for the parameter of said third signal so that the third signal parameter will be within such range when a multiple sheet condition has occurred; and
   f. comparison means for comparing such third electrical signal and reference signal parameters for producing an output indicating that a multiple sheet condition has occurred when the third parameter is within such reference signal parameter range.

5. Method for detecting a multiple sheet feed condition comprising:
   a. producing a time varying ultrasonic signal which impinges upon sheet(s) at a first position along a predetermined sheet feeding path;
   b. receiving a portion of the ultrasonic wave which impinged upon such sheet(s) and, in response thereto, producing a first time varying electrical signal; and
   c. providing an output when the phase of such first time varying electrical signal indicates a multiple sheet feed condition has occurred.

6. Method for detecting a multiple sheet feed condition comprising:
   a. producing a first time varying electrical signal at a predetermined frequency;
   b. producing a time varying ultrasonic signal at such predetermined frequency which impinges sheet(s) at a position along a predetermined path;
   c. receiving a portion of said ultrasonic signal which impinged upon said sheet(s) and, in response thereto, producing a second time varying electrical signal; and
   d. comparing such first and second electrical signals and producing an output when the phase difference between said signals indicates that a multiple sheet feed condition has occurred.

7. Method for determining the presence or absence of a sheet at a predetermined position comprising:
   a. directing a time varying ultrasonic signal to said predetermined position;
   b. receiving a portion of the ultrasonic signal coming from said predetermined position;
   c. comparing the phase of the directed and received ultrasonic signals; and
   d. producing an indication of the presence or absence of a sheet at said predetermined position in accordance with the differences in phase of said directed and received ultrasonic signals.

8. Method for determining whether or not a sheet is disposed at a predetermined position along a path comprising:
   a. producing a first time varying electrical signal at a predetermined frequency;
   b. producing a time varying ultrasonic signal having a frequency and phase which corresponds to that of said first signal;
   c. directing said ultrasonic signal to impinge upon a sheet if it were disposed at said predetermined position;
   d. receiving at least a portion of the ultrasonic signal at said predetermined position and, in response thereto, producing a second time varying electrical signal having a frequency and phase corresponding to said received ultrasonic signal; and
   e. comparing the phase relationship between the first and second electrical signals and in response thereto producing a manifestation of whether or not a sheet is disposed at the predetermined position.

* * * * *